United States Patent [19]

Kreft

[11] 4,348,732

[45] Sep. 7, 1982

[54] METHOD AND APPARATUS FOR ENGINE EXHAUST ANALYZER

[75] Inventor: Keith A. Kreft, Mount Prospect, Ill.

[73] Assignee: Sun Electric Corporation, Crystal Lake, Ill.

[21] Appl. No.: 116,406

[22] Filed: Jan. 29, 1980

[51] Int. Cl.³ .............................................. G01N 1/22
[52] U.S. Cl. .................................... 364/571; 364/424; 73/1 G; 73/23
[58] Field of Search ....................... 364/571, 497, 424; 73/1 G, 1 R, 23, 116, 117.1; 60/276

[56] References Cited

U.S. PATENT DOCUMENTS

| | | | |
|---|---|---|---|
| 3,593,023 | 7/1971 | Dodson et al. | 73/23 |
| 3,924,442 | 12/1975 | Kerho et al. | 73/23 |
| 3,973,848 | 8/1976 | Jowett et al. | 73/23 |
| 3,998,095 | 12/1976 | Tinkham et al. | 73/23 |
| 4,030,349 | 6/1977 | Blanke et al. | 73/23 |
| 4,094,187 | 6/1978 | Navarre, Jr. | 73/1 G |
| 4,160,373 | 7/1979 | Fastaia et al. | 73/23 |

Primary Examiner—Charles E. Atkinson
Assistant Examiner—Gary Chin
Attorney, Agent, or Firm—Allegretti, Newitt, Witcoff & McAndrews

[57] ABSTRACT

A processing unit for normalizing the output data of a gas analyzer in view of zero adjustment data and gain adjustment data formulated by the processing unit controlling air input and span reference simulation of a reference gas. A voltage reference generator is manually variable for calibrating the system while passing a known reference gas through the analyzer, in order to provide a scaling factor for use during output data adjustment. A hold switch is manually actuable by the operator for storing in memory the value of a gas analyzation voltage for permitting adjustment to the output data after the gas is removed from the cell of the analyzer.

19 Claims, 4 Drawing Figures

Fig. I (PRIOR ART)

METHOD AND APPARATUS FOR ENGINE EXHAUST ANALYZER

BACKGROUND OF THE INVENTION

The invention relates to a method and apparatus for calibrating a gas analyzer and, more particularly, the calibration of an automotive engine, exhaust analyzer.

Heretofore, a non-automatic calibration of an automotive exhaust analyzer required the operator to adjust two controls. One control varies a resistive potentiometer for zeroing the system display as the operator passes air through the analyzer. The second control also varies a potentiometer for adjusting system gain as the operator actuates a mechanical or electrical span reference to simulate a calibration gas passing through the analyzer.

The use of a span reference to simulate a calibration gas avoids the necessity of having an actual reference gas on hand for adjusting system gain. The span reference itself is variable by a third potentiometer for setting the value of the gas which the span reference is to simulate. The third potentiometer is set at the factory during manufacture of the analyzer; however, in certain cases, the span reference potentiometer may be accessible to the operator who is able to feed a known calibration gas through the analyzer for calibrating the span reference.

Attempting to make the calibration procedure easier for the operator and more reliable, an automatic calibration technique has been suggested wherein the final output of the analyzer is altered in view of calibration adjustment data formulated by the system. The operator actuates an instruction button for commanding the system to update the adjustment data. The automatic calibration technique utilizes a span reference instead of actual calibration gas, and requires three potentiometers for calibration of the span reference at the factory or by the operator who has access to actual calibration gas.

During calibration of the span reference, the most accurate calibration method occurs under a normal dynamic flow condition of the calibration gas through the analyzer. However, a large quantity of calibration gas is consumed during the time the operator is making the proper adjustment to the span reference.

To overcome consumption of the sample gas, the prior art has suggested a static flow condition, wherein the gas is injected into the analyzer and held statically allowing the operator to take his time in making the adjustment. However, this introduces calibration inaccuracies into the system due to drops in pressure and, hence, inaccuracies in the density of the gas in the analyzer with respect to the actual occurence of normal dynamic operating conditions.

It is, therefore, an object of the present invention to provide an improved calibration system for a gas analyzer.

It is another object of the present invention to provide a calibration system which includes a span reference and requires only a single operator adjustment for affecting calibration.

It is a further object of the present invention to provide a calibration system permitting consumption of a smaller amount of calibration gas during system calibration than, heretofore, realized.

It is yet another object of the present invention to permit adjustment to an analyzed reading after the gas has been removed from the analyzer cell.

SUMMARY OF THE INVENTION

A data processor normalizes analyzed gas output data from a gas analyzer system in view of error adjustment data formulated by the processor. An independent voltage generator is operator variable for providing an adjustment scalar for calibrating the system to permit accurate normalization by the processor.

A hold control is operator actuable for instructing the processor to store in memory the analyzed value of a calibration gas prior to processor normalization. The gas may then be removed from the analyzer cell, and the stored data operated upon by the processor.

DESCRIPTION OF THE PREFERRED EMBODIMENT

Figure 1:
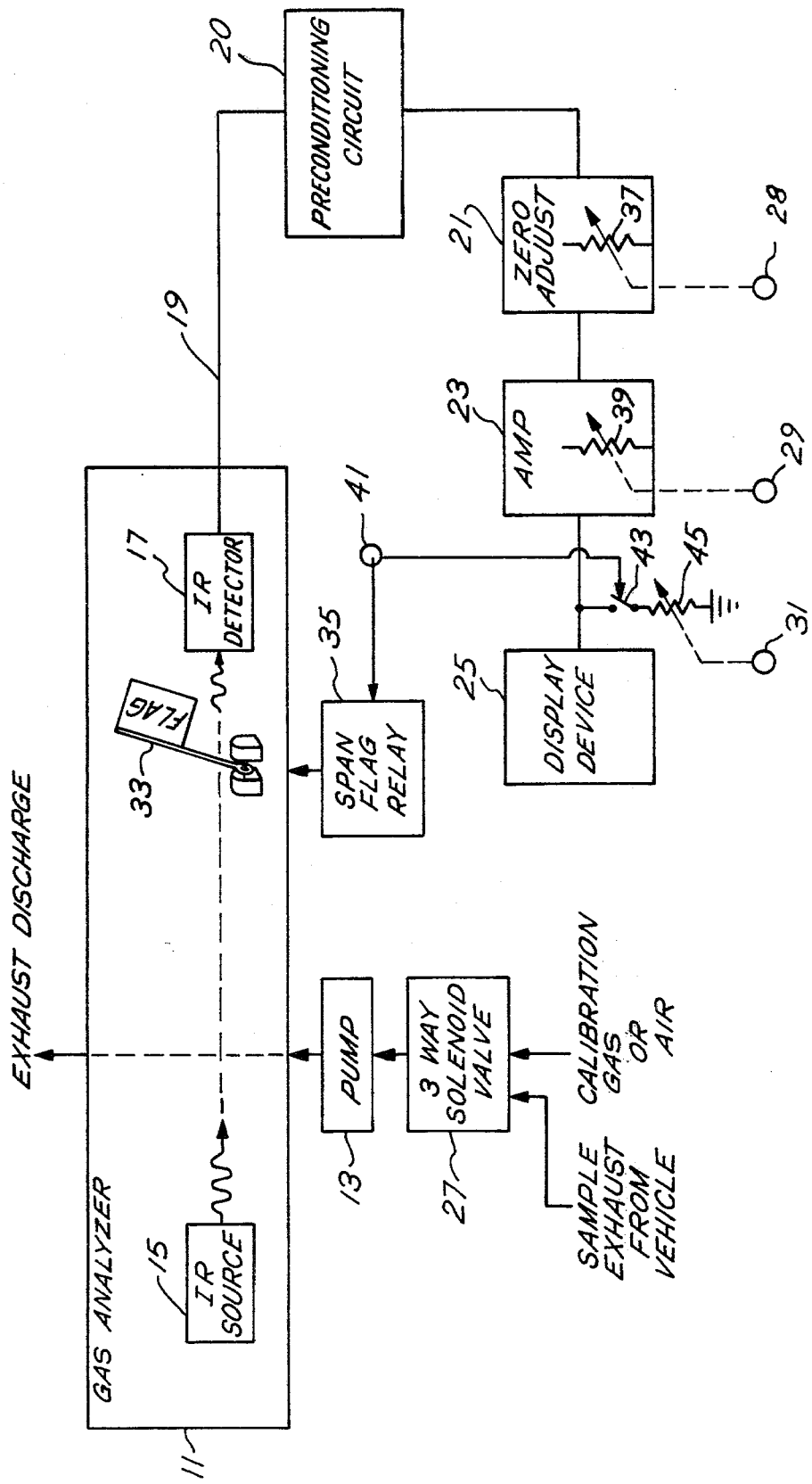
FIG. 1 is a block diagram and partial schematic diagram of a prior art non-automatic gas analyzer system.

Referring to FIG. 1, a prior art system over which the preferred embodiment is an improvement, includes a gas analyzer 11 for analyzing an exhaust gas from an automotive vehicle engine (not shown) as the gas is pumped through the analyzer via a pump 13. An infrared radiation source 15 projects a beam of radiation through the gas and onto an infrared detector 17. Detector 17 transduces the infrared energy emanating from source 15 to a voltage signal output developed along a conductor 19. Conductor 19 passes the voltage signal through a preconditioning circuit 20 which comprises a preamplifier circuit, an automatic gain control circuit, a circuit for referencing the voltage signal to ground and a demodulation circuit. After the voltage signal is conditioned by circuit 20, the resultant conditioned signal passes through a zero adjust circuit 21 and an amplifier circuit 23 prior to driving a display device 25. The gaseous and particulate matter contained in the exhaust gas absorbs infrared radiation as the gas passes through the infrared beam and accordingly changes the amount of energy detected by infrared detector 17. Thus, the signal output of detector 17 is indicative of the emissions in the exhaust gas being analyzed.

The prior art system of FIG. 1 is referred to hereinafter as a non-automatic calibration system, and an example of such a system is manufactured by SUN ELECTRIC CORPORATION, a corporation of Delaware, as Model EPA-75. The system of FIG. 1 is calibrated by two controls 28, 29 for respectively adjusting zero adjust circuit 21 and amplifier circuit 23. A third control 31, which may or may not be accessible to the operator, adjusts the displayed value of a span reference as described hereinafter. Zero adjust circuit 21 is adjusted for providing a zero display reading on display device 25 when air is passed through analyzer 11, for zeroing the system. The gain of amplifier 23 is adjusted by control 29 for providing a proper gas display reading on display device 25 as a known calibration gas is passed through the analyzer.

In order to provide input of air or a calibration gas into analyzer 11 for performing the calibration operation, a three-way valve 27 is utilized. The valve also permits entry of a sample exhaust gas from the engine during actual gas analyzation.

To avoid the use of an actual calibration gas each time the operator makes a gain adjustment, a mechanical span flag 33 is utilized as a span reference to simulate a reference gas. Span flag 33 is selectively operable by a span flag relay 35 for movement of flag 33 into the infrared radiation path for mechanically obstructing infrared rays for simulating a fixed absorption reference. Span flag 33 is calibrated by control 31 for setting the flag's display reading on display device 25 to a value equal to the calibration gas. The use of an actual calibration gas for calibrating flag 33 is performed at the factory during manufacture of the analyzer; however, the span flag may be calibrated in the field where the operator has a supply of a known calibration gas.

Control 28 operates a resistive potentiometer 37 of the zero adjustment circuit for affecting the voltage output of the preconditioning circuit 20, prior to amplification by amplifier 23. The operator passes air into the gas analyzer and turns control knob 28 until the voltage output of zero adjust circuit 21 causes display device 25 to display a value of zero.

Control 29 operates a resistive potentiometer 39 for varying the gain of amplifier 23. The operator sets the gain by actuating span flag 33 via a control button 41, for simulating a known gas. Control 29 is then turned by the operator until display device 25 displays a gas value representative of the gas simulated by flag 33.

When span flag 33 is actuated by control button 41 a switch 43 is closed in order to insert a resistive potentiometer 45 across the output of amplifier 23. Potentiometer 45 serves to attenuate the output reference voltage developed by flag 33 and is trimmed at the factory for internally setting the reference voltage developed by the flag.

To set the displayed value of the span flag, the system is first zeroed by feeding air into the analzyer and trimming zero adjust potentiometer 37. Thereafter, a known calibration gas is fed into the analyzer via three-way valve 27 and the gain of amplifier 23 is adjusted for providing an accurate display value representative of the known calibration gas. Thereafter, air is fed back into the analyzer and the span flag 33 is actuated. Resistor 45 is then trimmed for generating a display value representative of the known calibration gas. This procedure is performed at the factory for initially calibrating the span flag; however, an operator having a source of a calibration gas may perform the span flag calibration in the field.

After the calibration system of FIG. 1 was in use, an automatic calibration system was developed in the prior art for automatically calibrating the analyzer without need for the operator to adjust potentiometers 37, 39. Such a system is manufactured by SUN ELECTRIC CORPORATION, as Model, SUN 2001. The prior art automatic calibration system may be described in connection with the preferred embodiment of the present invention as illustrated in FIG. 2, which preferred embodiment is an improvement over the automatic calibration system of the prior art.

Figure 2:
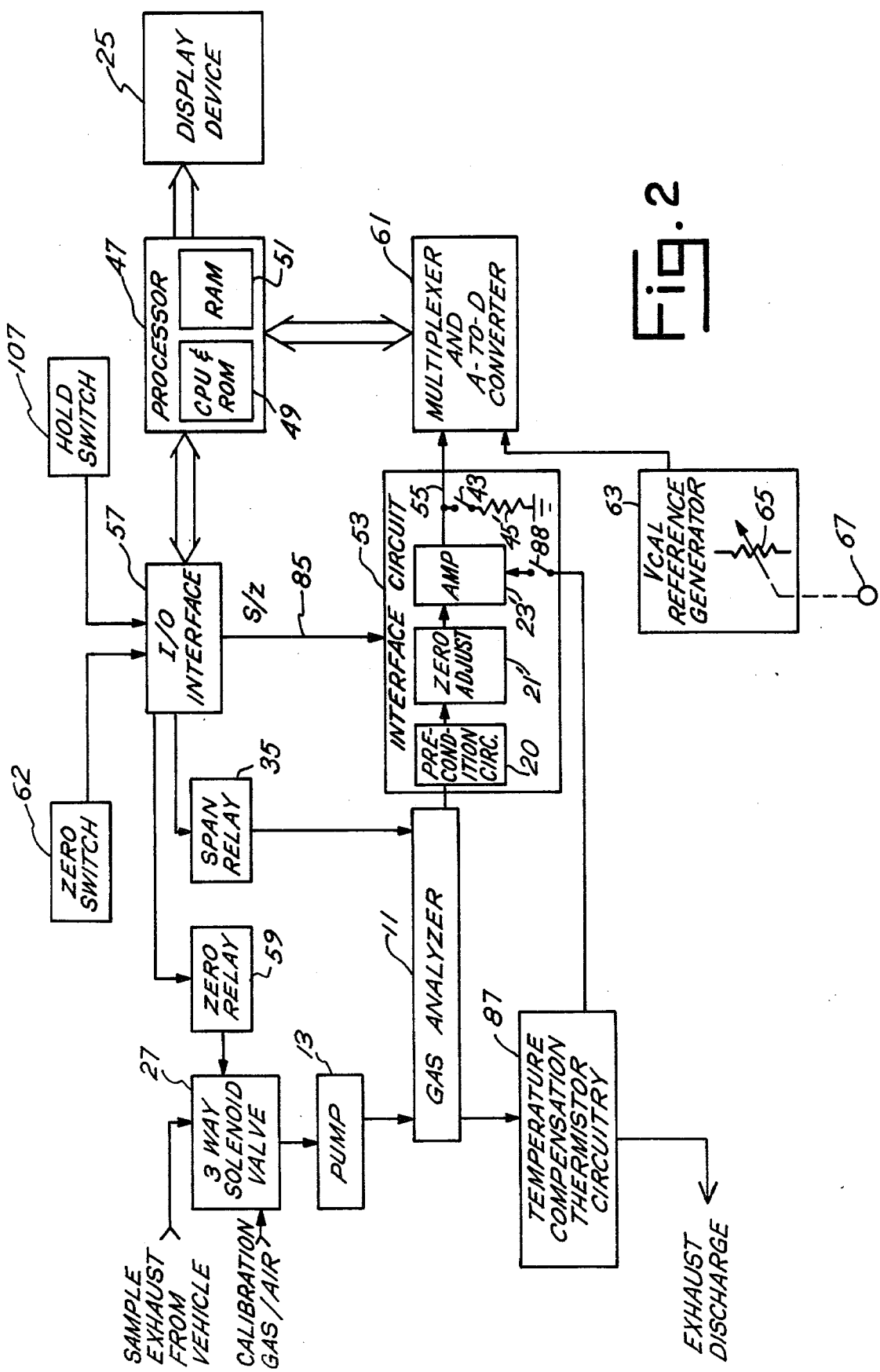
FIG. 2 is a block diagram and partial schematic of a preferred embodiment of a gas analyzer system of the present invention.

Like the system of FIG. 2, the automatic calibration system of the prior art includes a processor 47, comprising a CPU and Read-only memory 49 and random access memory 51, which performs the automatic calibration of the system. The prior art automatic system includes gas analyzer 11 connected to an interface circuit 53 which comprises the preconditioning circuit 20, the zero adjust circuit 21, the amplifier circuit 23 and the span switch 43 of FIG. 1, for producing a voltage output $V_{gas}$ on a conductor 55 during gas analyzation. Processor 47 reads the voltage output $V_{gas}$ on conductor 55 and computes a correction voltage $V_{norm}$ for driving display device vice 25. $V_{norm}$ serves to adjust $V_{gas}$ in view of zero adjustment data and gain adjustment data. The processor performs an automatic calibration by updating the zero adjustment and gain adjustment data, when instructed by the operator.

In order to perform the automatic calibration, the processor of the prior art system stores a zero adjust value, $V_{zero}$, and gain adjustment values, $V_{s/z}$ and $V_{span}$. The output voltage $V_{gas}$ is normalized by the processor using the zero adjustment data and the gain adjustment data for formulating a voltage display value, $V_{norm}$, for use to display a display reading of the analyzed gas.

The prior art automatic system calculates $V_{norm}$ as follows:

$$V_{norm} = \frac{(V_{gas} - V_{zero})}{(V_{span} - V_{s/z})} \cdot A,$$

where A is a constant.

Processor 47, of the prior art system, instructs gas input and span flag actuation for generating the adjustment data. Control signals are transmitted via an input/output interface 57 for operating a zero relay 59 to actuate valve 27 and for operating span relay 35 to actuate the span flag. The processor retrieves gas value information, $V_{gas}$, from interface circuit 53 via a multiplexer/A-to-D converter circuit 61.

As will be appreciated, the automatic calibration of the prior art system by processor 47 utilizes span flag 33 for simulating a reference gas in order to obtain gain adjustment data. However, the calibration of span flag 33 by the prior art automatic system must be manually performed using the three potentiometers of FIG. 1. The manual calibration must be performed at the factory during manufacture, which requires labor expense and component cost of the three potentiometers.

The automatic prior art system is manually calibrated in the same manner as the non-automatic system of FIG. 1, in which potentiometer 37 is adjusted to zero the system; thereafter, a calibration gas is fed into the gas analyzer and potentiometer 39 is adjusted for providing the proper gain; thereafter, span flag 33 is actuated and potentiometer 45 is adjusted for calibrating the voltage output provided by the span flag. Where the calibration of the span flag is performed in the field, these manual steps must be performed by the operator. A zero switch 62 is provided for permitting the operator to actuate zero 59 via input/output interface 57, for feeding calibration gas or air into analyzer 11.

The preferred embodiment of the present invention places fixed resistors in place of the three potentiometers 37, 39 and 45, for forming a new zero adjust circuit 21', an amplifier 23' and a new resistor 45', as shown in FIG. 2. The embodiment also adds a variable reference voltage generator 63 for providing a sole adjustment to be made in calibrating the system. To calibrate the system, a calibration gas is fed into analyzer 11 and reference generator 63 is adjusted to a voltage $V_{cal}$ at which the display output represents the actual calibration gas fed into analyzer 11. As will be appreciated, values for $V_{zero}$, $V_{s/z}$, $V_{span}$ and $V_{cal}$ must be stored by processor 47 prior to adjustment of generator 63.

In the preferred embodiment, reference voltage generator 63 includes a single potentiometer 65 for manual adjustment by a control 67 for providing a variable voltage output, $V_{cal}$, to multiplexer/A-to-D converter 61. As will suggest itself, other than a potentiometer may be utilized to construct a variable voltage source; however, generator 63 must be non-volatile for memorizing the output $V_{cal}$ between power shut-downs and power turn-ons.

Processor 47 of the preferred embodiment of the present invention calculates the display reading $V_{norm}$ in terms of $V_{cal}$, according to the following formula:

$$V_{norm} = \frac{(V_{gas} - V_{zero})}{(V_{span} - V_{s/z})} \cdot \frac{(V_{cal} + A_1)}{A_2},$$

where $A_1$ and $A_2$ are constants.

Figure 3:
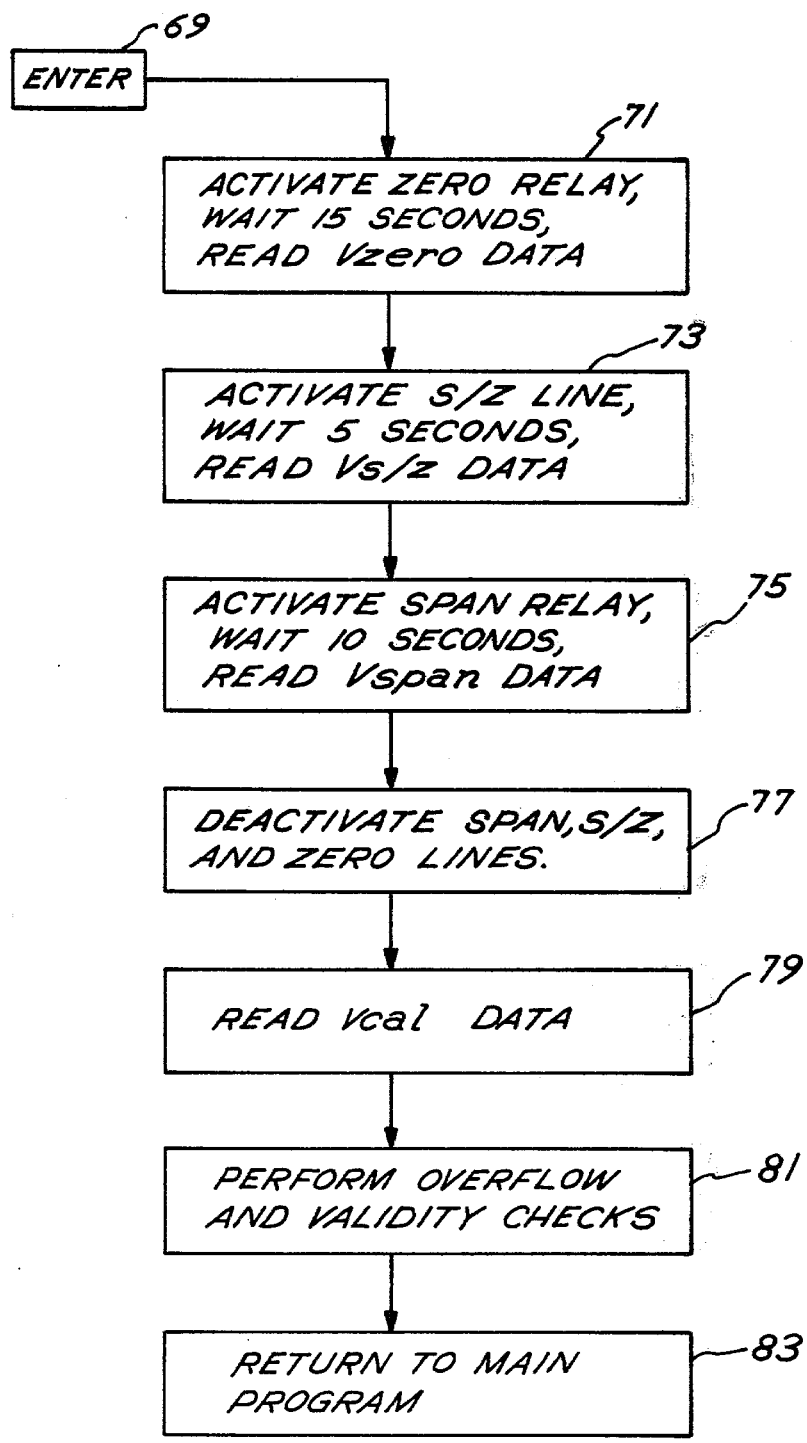
FIG. 3 is a flow diagram of a normalization routine to be executed by the processor of the analyzer system of FIG. 2.

Referring to FIG. 3, a zero and span drift normalization routine is illustrated which is performed by processor 47 after a warm-up period following power initialization of the system. The routine of FIG. 3 is periodically performed by the operator at his discretion to correct for possible short-term voltage output drifts of the gas analyzer due to fluctuations in line voltage, ambient operating temperatures, etc. The routine gathers and stores the voltages $V_{zero}$, $V_{s/z}$, $V_{span}$ and $V_{cal}$, to be utilized in the computation of the display gas reading, $V_{norm}$.

As the routine of FIG. 3 is entered at 69, a plurality of steps 71–83 are executed by processor 47. The execution of step 71 activates zero relay 59 (FIG. 2) and purges gas analyzer 11 with air. The processor waits 15 seconds to ensure proper purging; then the voltage output of the gas analyzer is processed by interface circuit 53 and fed to multiplexer/A-to-D converter 61 where it is read and stored by processor 47 as $V_{zero}$.

Thereafter, execution of step 73 causes activation of a conductor 85 via input/output interface 57 for closing span switch 43 of interface circuit 53. Also, activation of conductor 85 disconnects a temperature compensation thermistor circuitry 87 from amplifier 23' of the interface circuit, via a switch 88. Temperature compensation circuitry, which also forms a part of the prior art systems, includes a thermistor (not shown) which is located in the gas stream of gas analyzer 11 for monitoring gas temperature. Circuitry 87 responds to temperature of the analyzed gas for controlling gain in the amplifier 23'. The disconnection of circuitry 87 permits development of gain adjustment data without regard to the temperature reading in analyzer 11. The actuation of conductor 85 with air passing through analyzer 11, provides a voltage output from interface circuit 53 which is read and stored by processor 47 as $V_{s/z}$, which represents an attenuated $V_{zero}$ reading.

Thereafter, step 75 is executed activating span relay 35 for moving span flag 33 into the radiation path. Span switch 43 continues to be closed and air continues to be passed through analyzer 11. The output of the gas analyzer is again processed by interface circuit 53 (without temperature compensation circuitry 87 connected) and read and stored in memory by processor 47 as $V_{span}$. The zero relay and span relay are then deactivated, switch 43 is opened and switch 88 is closed, returning the system to a state for analyzation (step 77).

Step 79 is then executed for reading and storing the voltage $V_{cal}$ by processor 47. Thereafter, at step 81, the processor performs an overflow check and a validity check, in which the voltage data retrieved in the calibration update is checked for errors by determining whether the data lies within a proper range of values and whether the data is valid in view the total data values retrieved. Return is then made to the main program via step 83.

Figure 4:
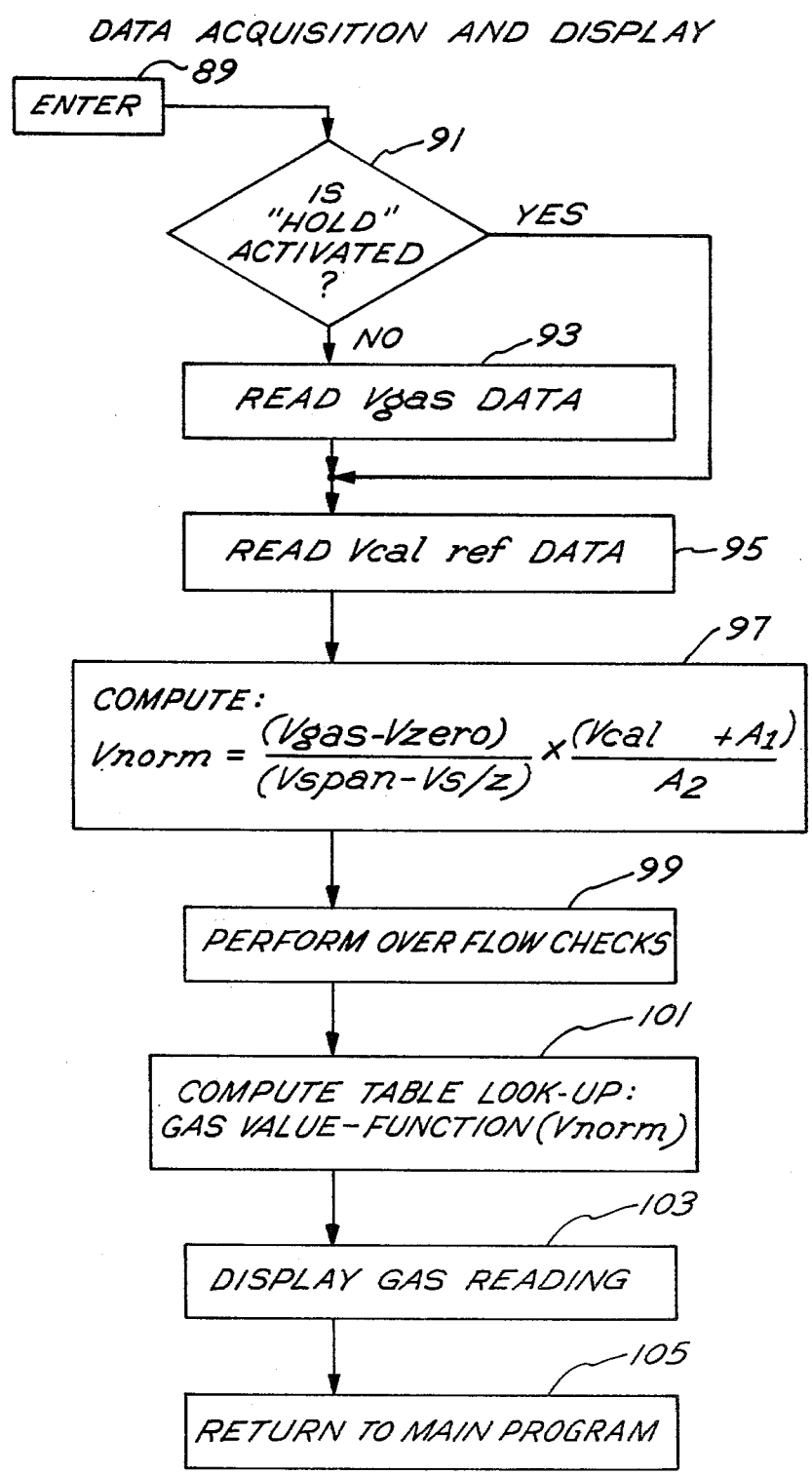
FIG. 4 is a flow diagram of a data acquisition and display routine to be executed by the processor of the analyzer system of FIG. 2.

Referring to FIG. 4, a data acquisition and display routine is illustrated which is performed by the processor every x number of milliseconds for generating display data. The routine is entered at 89 and a plurality of steps 91–105 are executed.

Execution of step 91 performs a check on a hold switch 107 (FIG. 2) for determining whether hold switch 107 has been actuated by the operator. Hold switch 107 is a bi-state switching device actuable by the operator for generating a digital signal output to input-/output interface 57 for transmittal to processor 47. The operator's actuation of hold switch 107 provides an instruction to the system to store the $V_{gas}$ output of the calibration gas passing through analyzer 11, so that the calibration of the system can be performed on the stored $V_{gas}$ and the actual calibration gas may be discontinued from input to analyzer 11.

If the hold switch is not activated, step 93 updates the $V_{gas}$ reading by reading the voltage output from interface circuit 53. The temperature compensation circuitry 87 is connected during calibration gas input.

The calibration reference voltage $V_{cal}$ is thereafter read at step 95, from reference generator 63, and $V_{norm}$ is calculated at step 97. $V_{norm}$ is the normalized $V_{gas}$ reading which is obtained by correcting for zero drift by subtracting the $V_{zero}$ voltage and correcting for gas analyzer gain or span drift by dividing by $V_{span} - V_{s/z}$. The zero and gain corrected voltage is then scaled by $V_{cal}$. $A_1$ and $A_2$ are constants in software which are utilized to scale the multiplier $(V_{cal} + A_1)/A_2$ in view of the range of voltages generated by reference generator 63.

At step 99, $V_{norm}$ is checked to see if it is within a predetermined range. $V_{norm}$ is then utilized to determine the gas value which will be displayed by interpolation from a look up table, at step 101. The gas value is displayed step 103, and control is returned to the main program, step 105.

As the data acquisition and display routine of FIG. 4 is continuously performed, the $V_{gas}$ and $V_{cal}$ data are continuously updated along with the displayed gas reading. Upon activation of the hold switch 107, the $V_{gas}$ data is no longer updated. The routine is still continuously performed using the last stored $V_{gas}$ data reading. This allows any voltage output of the gas analyzer system resulting from the introduction of a gas into the analyzer to be stored, and the resulting gas value which is displayed to be adjusted (calibrated) by varying $V_{cal}$. The $V_{gas}$ reading can be captured under dynamic flow conditions and then the gas source removed before the actual adjustment is performed for calibrating the system.

It should be understood, of course, that the foregoing relates to a preferred embodiment of the present invention and that modifications may be made therein without departing from the spirit or scope of the invention as set forth in the appended claims.

What is claimed is:

1. A gas analyzation system for analyzing an unknown gas, comprising:
   gas analyzing means for receiving an unknown gas to be analyzed and generating an electrical signal output representative of the analyzation of the unknown gas;
   span reference means selectively actuable for simulating a reference gas, said gas analyzer means cooperating with said span reference means for generating a reference signal output representative of said reference gas in response to actuation of said span reference means;
   display means responsive to display data for visually displaying an indication of gas analyzation;
   data entry means for inputing a sole scaler data, said data entry means being controllable for selectively changing said sole scaler data; and
   processing means including memory,
   (i) for receiving said electrical signal output representative of the analyzation of the unknown gas and converting the same to gas data,
   (ii) for actuating said span reference means for generating a reference signal output, for receiving said reference signal output and converting the same to reference data,
   (iii) for reading said sole scalar data,
   (iv) for generating display data from said gas data by adjusting said gas data in view of said reference data and said sole scalar data, and
   (v) for transmitting said display data to said display device.

2. A gas analyzation system according to claim 1 wherein said electrical signal output representative of an unknown gas in an analog signal; and wherein said processing means includes an analog-to-digital converter for converting said electrical signal output representative of the unknown gas to said gas data.

3. A gas analyzation system according to claim 1 wherein said gas analyzing means includes:
   a gas analyzer for receiving a gas to be analyzed and generating an output analog signal indicative of an analyzation of the gas;
   amplifier means for amplifying said output analog signal at a fixed gain; and
   attenuation means selectively actuable for attenuating the output of said amplifier means, said attenuation means having a fixed attenuation.

4. A gas analyzation system according to claim 3 and further including:
   gas input control means selectively actuable for passing either an unknown gas or air into said gas analyzer; and
   wherein said gas analyzer receives said unknown gas passing from said gas input control means, for generating an electrical signal output representative of the analyzation of said unknown gas, and
   wherein said gas analyzer receives said air passing from said gas input control means, for generating an electrical signal output representative of the analyzation of air; and
   wherein said processing means actuates said gas input control means, for passing air into said gas analyzer for generating a said electrical signal output representative of the analyzation of air, said processing means for processing said electrical signal output representative of the analyzation of air for generating zero gas data, said processing means storing said zero gas data in memory, and said processing means adjusting said gas data in view of said zero gas data for generating said display data.

5. A gas analyzation system according to claim 4 wherein said processing means actuates both said gas input control means and said attenuation means, for passing air into said gas analyzer for generating a said electrical signal output representative of the analyzation of air, said processing means for processing said electrical signal output representative of the analyzation of air for generating attentuated zero gas data, said processing means storing said attenuated zero gas data in memory, and said processing means adjusting said gas data in view of said attenuated zero gas data for generating said display data.

6. A gas analyzer according to claim 1 and further including:
   gas input control means selectively actuable for passing either an unknown gas or air into said gas analyzation means;
   and wherein said gas analyzation means receives said unknown gas passing from said gas input control means, for generating an electrical signal output representative of the analyzation of said unknown gas, and wherein said gas analyzer receives said air passing from said gas input control means, for generating an electrical signal output representative of the analyzation of air;
   and wherein said processing means actuates said gas input control means for passing air into said gas analyzation means for causing said gas analyzing means to generate an electrical signal output representative of the analyzation of air, said processing means processing said electrical signal output representative of the analyzation of air for generating zero gas data, said processing means storing said zero gas data in memory, and said processing means adjusting said gas data in view of said zero gas data for generating said display data.

7. A gas analyzation system according to claim 1 wherein said span reference means includes a mechanical flag means for providing a mechanical obstruction within said gas analyzing means for simulating said reference gas.

8. A gas analyzation system according to claim 1 wherein said data entry means includes a voltage source manually controllable for generating a variable voltage output.

9. A gas analyzation system according to claim 8 wherein said data entry means includes a resistive potentiometer manually adjustable for varying said voltage output.

10. A gas analyzation system according to claim 9 wherein said processing means retrieves said voltage output, converts said voltage output to a digital signal and stores said digital signal in memory.

11. A gas analyzation system for analyzing an unknown gas, comprising:
   gas analyzing means for receiving a gas to be analyzed and generating an electrical signal output representative of the analyzation of the gas;
   gas input control means selectively actuable for passing either an unknown gas or air into said gas analyzing means;
   display means responsive to display data for visually displaying an indication of gas analyzation;
   data entry means for inputting a sole scalar data, said data entry means being controllable for selectively changing said sole scalar data; and processing means including memory,
(i) for actuating said gas input control means for passing air into said gas analyzing means, for causing said gas analyzing means to generate an electrical signal output representative of the analyzation of air, said processing means for processing said electrical signal output representative of the analyzation of air for generating zero adjustment data, said processing means storing said zero adjustment data in memory;
(ii) for reading said sole scalar data;
(iii) for actuating said gas input control means for passing an unknown gas into said gas analyzing means, for causing said gas analyzing means to generate an electrical signal output representative of the analyzation of an unknown gas and for converting said electrical signal output representative of the analyzation of an unknown gas to gas data, said processing means for generating display data from said gas data by adjusting said gas data in view of said zero adjustment data and said sole scalar data; and
(iv) for transmitting said display data to said display device for affecting visual display of an indication of the analyzation of the unknown gas.

12. A gas analyzation system according to claim 11 wherein said data entry means for inputting a sole scalar data includes a voltage source manually controllable for generating a variable voltage output.

13. A gas analyzation system according to claim 12 wherein said means for inputting a sole scalar data includes a resistive potentiometer manually adjustable for varying said voltage output.

14. A gas analyzation system according to claim 13 wherein said processing means retrieves said voltage output, converts said voltage output to a digital signal and stores said digital signal in memory.

15. A gas analyzation system formalizing an unknown gas, the improvement wherein the system is calibrated using a sole manually variable control, a known calibration gas and air comprising:
gas analyzing means for receiving gas and generating an electrical signal output representative of the analyzation of the gas;
input means for passing air into said gas analyzing means or for passing a known calibration gas into said gas analyzing means;
display means responsive to display data for visually displaying an indication of gas analyzation, said display means for displaying an indication of the known analyzation of said known calibration gas;
a sole manually variable control for generating variable scalar data, said control manually variable for adjusting the display of said display device for indicating said known analyzation; and
processing means including memory
(i) for processing said electrical signal output when air is passing into said gas analyzation means, for generating zero adjustment data, said processing means storing said zero adjustment data in memory;
(ii) for reading said scalar data;
(iii) for processing said signal output when a calibration gas is passing into said gas analyzing means, for generating gas data, said processing means generating display data from said gas data by adjusting said gas data in view of said zero adjustment data and said scalar data;
(iv) for transmitting said display data to said display device for affecting visual display of an indication of the analyzation of the known calibration gas; and
(v) for repeatedly reading said scalar data for repeatedly generating display data, for varying said indication in accordance with variation in said scalar data.

16. A gas analyzation system for analyzing an unknown gas, comprising:
gas analyzing means for receiving gas and generating an electrical signal output representative of the analyzation of the gas;
input means for passing gas into said gas analyzing means;
display means responsive to display data for visually displaying an indication of gas analyzation;
a hold actuator manually actuable for generating a hold signal; and
processing means including memory,
(i) for processing said electrical signal output when gas is passing into said gas analyzing means, for generating gas data, said processing means for storing said gas data in memory;
(ii) for generating display data from said gas data;
(iii) for transmitting said display data to said display device for affecting visual display of an indication of the analyzation of the gas; and
(iv) for repeatedly processing said electrical signal output for updating said gas data for affecting said visual display accordingly, ssid processing means responsive to said hold signal for discontinuing repeated processing of said electrical signal output for maintaining the value of said gas data as stored in memory.

17. A gas analyzation sysem according to claim 16 wherein said processing means generates error drift data, said processing means generating said display data from said gas data as a function of said error drift data, and wherein said processing means repeatedly updating said display data during generation of said hold signal.

18. A gas analyzation system according to claim 17 including means for providing scalar data, said means for providing scalar data being controllable for varying said scalar data; and wherein said processing means generates display data from said gas data as a function of said error drift data and said scalar data.

19. A gas analyzation system according to claim 18 and further including a sole control knob connected to said means for providing scalar data, said control knob manually adjustable for varying said display data.

* * * * *